United States Patent [19]

Maignan et al.

[11] Patent Number: 4,833,240

[45] Date of Patent: May 23, 1989

[54] BICYCLIC AROMATIC DERIVATIVES, METHOD FOR PREPARING THEM, AND THEIR USE IN HUMAN AND VETERINARY MEDICINE AND IN COSMETICS

[75] Inventors: Jean Maignan, Tremblay les Gonesse; Gérard Lang, Saint Gratien; Gérard Malle, Villiers sur Morin; Serge Restle, Aulnay sous Bois; Braham Shroot, Antibes, all of France

[73] Assignee: Centre International de Recherches Dermatologiques (CIRD), Valbonne, France

[21] Appl. No.: 74,969

[22] Filed: Jul. 17, 1987

[30] Foreign Application Priority Data

Jul. 17, 1986 [FR] France ................................ 86 10423

[51] Int. Cl.$^4$ ................. A61K 31/045; A61K 31/123; A61K 1/15; A61K 1/185
[52] U.S. Cl. .................................... 536/55.2; 514/54; 514/62; 424/70; 560/8; 560/100
[58] Field of Search .................... 536/55.2; 514/54, 62; 560/100, 8; 424/70

[56] References Cited

U.S. PATENT DOCUMENTS 3,763,233 10/1973 Houlihan et al. .................... 564/47

FOREIGN PATENT DOCUMENTS 0123535 10/1984 European Pat. Off. .

*Primary Examiner*—Ronald W. Griffin
*Attorney, Agent, or Firm*—Cushman, Darby & Cushman

[57] ABSTRACT

Bicyclic aromatic compounds, having the following formula:

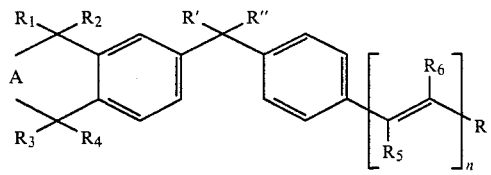

in which:
n=0 or 1;
R' represents H, OH, $C_1$-$C_4$ alkoxy or $C_1$-$C_4$ acyloxy;
R" represents H or $C_1$-$C_4$ alkoxy;
or R' and R" taken together form an oxo (=O), methano (=$CH_2$) or hydroximino (=N—OH) radical;
R represents —$CH_2OH$ or —$COR_7$;
$R_7$ represents H, $OR_8$, or

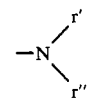

$R_8$ represents H, $C_1$-$C_4$ alkyl, monohydroxyalkyl, polyhydroxyalkyl, aryl or aralkyl, optionally substituted, a sugar residue or

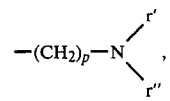

where p is 1, 2 or 3 and r' and r" represent H, lower alkyl, monohydroxyalkyl, optionally interrupted by a heteroatom, polyhydroxyalkyl, optionally substituted aryl or benzyl, an amino acid residue or an aminated sugar residue or taken together with the nitrogen atom to which they are attached form a heterocycle;
A represents methylene or dimethylene, substituted or not with lower alkyl,
$R_1$, $R_2$, $R_3$ and $R_4$ represent H or lower alkyl,
$R_1$ and $R_3$ taken together are capable of forming a methylene or dimethylene radical, when A represents dimethylene;
$R_5$ and $R_6$ represent H or methyl,
and the salts of said compounds, as well as their optical and geometric isomers.

This active compound is employed in pharmaceutical or cosmetic preparations.

29 Claims, No Drawings

BICYCLIC AROMATIC DERIVATIVES, METHOD FOR PREPARING THEM, AND THEIR USE IN HUMAN AND VETERINARY MEDICINE AND IN COSMETICS

The subject of the present invention is novel bicyclic aromatic derivatives, the method for preparing them, and their use in human and veterinary medicine and in cosmetics.

The compounds according to the invention exhibit an activity in the topical and systemic treatment of dermatological conditions associated with a keratinization disorder (differentiation/proliferation) and dermatological (or other) conditions having an inflammatory and/or immunoallergic component, and in the treatment of degenerative diseases of the connective tissue, as well as an anti-tumoral activity.

These compounds can also be utilized in the treatment of cutaneous or respiratory atrophy and of rheumatoid psoriasis.

These compounds also exhibit good activity against the germs involved in acne.

Finally, they have an application in the opthalmological field, in particular in the treatment of corneopathies.

The bicyclic aromatic derivatives according to the invention may be represented by the following general formula:

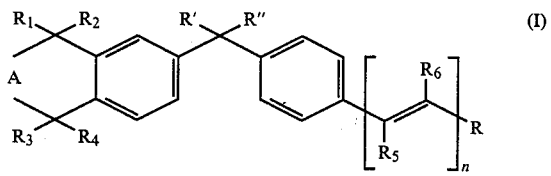

in which:

$n = 0$ or $1$;

R' represents a hydrogen atom, an OH radical, an alkoxy radical having from 1 to 4 carbon atoms, or an acyloxy radical having from 1 to 4 carbon atoms;

R'' represents a hydrogen atom or an alkoxy radical having from 1 to 4 carbon atoms;

or R' and R'' taken together form an oxo (=O), methano (=CH$_2$) or hydroximino (=N—OH) radical;

R represents the radical —CH$_2$OH or the radical —COR$_7$;

R$_7$ presents a hydrogen atom, the radical —OR$_8$ or the radical

in which R$_8$ represents a hydrogen atom, an alkyl radical having from 1 to 20 carbon atoms, a monohydroxyalkyl, polyhydroxyalkyl, aryl or aralkyl radical, optionally substituted, or a sugar residue or the radical

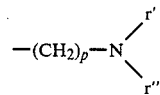

where p is 1, 2 or 3 and r' and r'' represent hydrogen, lower alkyl, monohydroxyalkyl optionally interrupted by a heteroatom, polyhydroxyalkyl, optionally substituted aryl or benzyl, amino acid residue, or aminated sugar residue, or taken together form a heterocycle with the nitrogen atom to which they are attached;

A represents methylene or dimethylene, whether or not substituted with a lower alkyl radical;

R$_1$, R$_2$, R$_3$ and R$_4$ represent hydrogen or lower alkyl;

R$_1$ and R$_3$ taken together being capable of forming a methylene or dimethylene radical, when A represents a dimethylene radical;

R$_5$ and R$_6$ represent hydrogen or methyl;

and the salts of said compounds, as well as their optical and geometric isomers.

The term lower alkyl means an alkyl having from 1 to 6 carbon atoms.

Representative lower alkyl radicals and those having up to 20 carbon atoms include methyl, ethyl, isopropyl, butyl, tert. butyl, 2-ethylhexyl, isooctyl, dodecyl, hexadecyl and octadecyl.

The term monohydroxyalkyl means a radical having from 2 to 6 carbon atoms, in particular 2-hydroxyethyl, 2-hydroxypropyl or 2-hydroxyethoxyethyl.

The term polyhydroxyalkyl means a radical containing from 3 to 6 carbon atoms and 2 to 5 hydroxyl groups, such as 2,3-dihydroxypropyl and 1,3-dihydroxy-2-propyl radicals or pentaerythritol residue.

As the alkoxy radical having from 1 to 4 carbon atoms, methoxy, isopropoxy, butoxy or tert. butoxy can be mentioned.

The term aryl means phenyl, optionally substituted with at least one halogen atom, —OH, —NO$_2$, lower alkyl, trifluoromethyl or a carboxylic acid function.

The benzyl radical and the phenethyl radical can be mentioned as a preferred aralkyl radical.

The term sugar residue means a residue derived from glucose, mannose, erythrose or galactose, for example.

Representative aminated sugar residues include those derived from glucosamine, galactosamine, mannosamine or meglumine.

When the radicals r' and r'' taken together form a heterocycle with the nitrogen to which they are attached, the heterocycle is preferably piperidino, piperazino, morpholino, pyrrolidino or 4-(2-hydroxyethyl) piperazino.

When the compounds according to the invention are in the form of salts, these may either be salts of an alkali metal or alkaline earth metal, or of zinc, or an organic amine when they include at least one free acid function, or salts of a mineral or organic acid, in particular hydrochloric, hydrobromic or citric acid, when they include at least one amine function.

As a function of formula I above, the compounds of the present application can be either bicyclic benzoic derivatives of formula II, or bicyclic cinnamic derivatives of formula III:

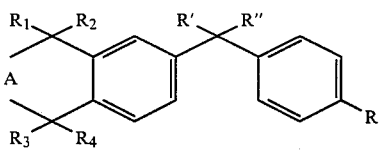 (II)

in which:

A, R, $R_1$–$R_4$, R' and R" have the same meanings as those provided above for formula I.

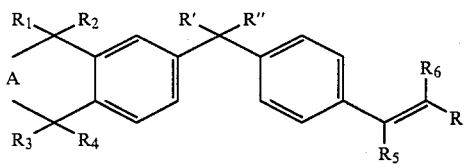 (III)

in which:

A, R, $R_1$–$R_6$, R' and R" have the same meanings as those provided above for formula I.

Among the compounds of formulas II and III that are particularly preferable according to the invention, those corresponding to the following formulas IV and V can be cited:

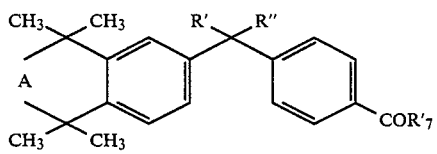 (IV)

in which:

A represents the radical $CH_3$—CH< or dimethylene;

R' represents OH and R" represents hydrogen, or R' and R", taken together, form an oxo radical (=O); and $R'_7$ represents hydrogen, —$OR'_8$, or

$R'_8$ represents hydrogen or lower alkyl;

r' represents hydrogen and r" represents lower alkyl or substituted phenyl, or r' and r" taken together form a 4-(2-hydroxyethyl) piperazino radical; and

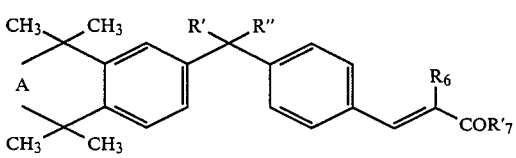 (V)

in which:

A represents $CH_3$—CH< or dimethylene,

R' represents OH and R" represents hydrogen, or R' and R", taken together, form an oxo radical (=O);

$R_6$ represents hydrogen or methyl, and $R'_7$ represents —$OR'_8$ or

$R'_8$ represents hydrogen or lower alkyl;

r' represents hydrogen and r" represents lower alkyl.

Repesentative compounds of formula I according to the invention include the following in particular:

(1) methyl (5,5,8,8-tetramethyl-5,6,7,8-tetrahydro-2-naphthyl)-4-carbonyl benzoate;

(2) (5,5,8,8-tetramethyl-5,6,7,8-tetrahydro-2-naphthyl)-4-carbonyl benzoic acid;

(3) (5,8-methano-5,6,7,8-tetrahydro-2-naphthyl)-4-carbonyl benzaldehyde;

(4) (5,5,8,8-tetramethyl-5,6,7,8-tetrahydro-2-naphthyl)-4-carbonyl benzaldehyde;

(5) methyl (1,1,2,3,3-pentamethyl-5-indanyl)-4-carbonyl benzoate;

(6) (1,1,2,3,3-pentamethyl-5-indanyl)-4-carbonyl benzoic acid;

(7) (1,1,2,3,3-pentamethyl-5-indanyl)-4-carbonyl benzaldehyde;

(8) 1-(1,1,2,3,3-pentamethyl-5-indanyl)-1-(4-hydroxymethylphenyl) methanol;

(9) (5,5,8,8-tetramethyl-5,6,7,8-tetrahydro)-2-naphthyl-4-hydroxymethyl benzoic acid;

(10) (1,1,2,3,3-pentamethyl-5-indanyl)-4-hydroxymethyl benzoic acid;

(11) methyl (1,1,2,3,3-pentamethyl-5-indanyl)-4-hydroxymethyl benzoate;

(12) N-ethyl(5,5,8,8-tetramethyl-5,6,7,8-tetrahydro-2-naphthyl)-4-carbonyl benzamide;

(13) N-ethyl (1,1,2,3,3-pentamethyl-5-indanyl)-4-carbonyl benzamide;

(14) ethyl trans-(5,8-methano-5,6,7,8-tetrahydro-2-naphthyl)-4-carbonyl cinnamate;

(15) trans-(5,8-methano-5,6,7,8-tetrahydro-2-naphthyl)-4-carbonyl cinnamic acid;

(16) ethyl trans-(5,5,8,8-tetramethyl-5,6,7,8-tetrahydro-2-naphthyl)-4-carbonyl cinnamate;

(17) trans-(5,5,8,8-tetramethyl-5,6,7,8-tetrahydro-2-naphthyl)-4-carbonyl cinnamic acid;

(18) ethyl trans-(5,5,8,8-tetramethyl-5,6,7,8-tetrahydro-2-naphthyl)-4-carbonyl-α-methyl cinnamate;

(19) trans-(5,5,8,8-tetramethyl-5,6,7,8-tetrahydro-2naphthyl)-4-carbonyl-α-methyl cinnamic acid;

(20) ethyl trans-(1,1,2,3,3-pentamethyl-5-indanyl)-4-carbonyl-α-methylcinnamate;

(21) trans-(1,1,2,3,3-pentamethyl-5-indanyl)-4-carbonyl-α-methyl cinnamic acid;

(22) ethyl trans-(5,5,8,8-tetramethyl-5,6,7,8-tetrahydro-2-naphthyl)-4-hydroxymethyl-α-methyl cinnamate;

(23) trans-(5,5,8,8-tetramethyl-5,6,7,8-tetrahydro-2-naphthyl)-4-hydroxymethyl-α-methyl cinnamic acid;

(24) N-ethyl-trans-(5,5,8,8-tetramethyl-5,6,7,8-tetrahydro-2-naphthyl)-4-hydroxymethyl-α-methyl cinnamide;

(25) N-ethyl-trans-(5,5,8,8-tetramethyl-5,6,7,8-tetrahydro-2-naphthyl)-4-carbonyl-α-methyl cinnamide;

(26) N-ethyl-trans-(1,1,2,3,3-pentamethyl-5-indanyl)-4-carbonyl-α-methyl cinnamide;

(27) ethyl trans-(5,5,8,8-tetramethyl-5,6,7,8-tetrahydro-2-naphthyl)-4-hydroxymethyl cinnamate;

(28) trans-(5,5,8,8-tetramethyl-5,6,7,8-tetrahydro-2-naphthyl)-4-hydroxymethyl cinnamic acid;

(29) 4'-(2-hydroxyethyl)piperazino(5,5,8,8-tetramethyl-5,6,7,8-tetrahydro-2-naphthyl) 4-carbonyl benzamide;

(30) N-(3,5-ditrifluoromethyl-1-phenyl)-(5,5,8,8-tetramethyl-5,6,7,8-tetrahydro-2-naphthyl)-4-carbonyl benzamide.

The subject of the present invention also relates to a method for preparing the compounds of formula I.

These compounds can be obtained by various methods, depending on their structure. The compounds of formula II may advantageously be prepared, for example, in accordance with the following reaction scheme:

The 4-alkoxycarbonyl-2-benzoic acid chloride (1) is obtained starting with an alkyl paraformyl benzoate that is oxidized in an acid corresponding to the use of a Jones reagent, and then is converted into acid chloride by the action of thionyl chloride, by the standard method for preparing acid chlorides.

Among the starting materials of formula (2), tetraline and indane are commercially available. 5,5,8,8-tetramethyl-5,6,7,8 tetrahydronaphthalene (or 5,5,8,8 tetramethyltetraline) is prepared by the method described by H.Q. Bruson and J.W. Kroger, J. Am. Chem. Soc. 62, 36–44 (1940). 5,8-methano -5,6,7,8 tetrahydronaphthalene is obtained by the method describsd in J. Org.

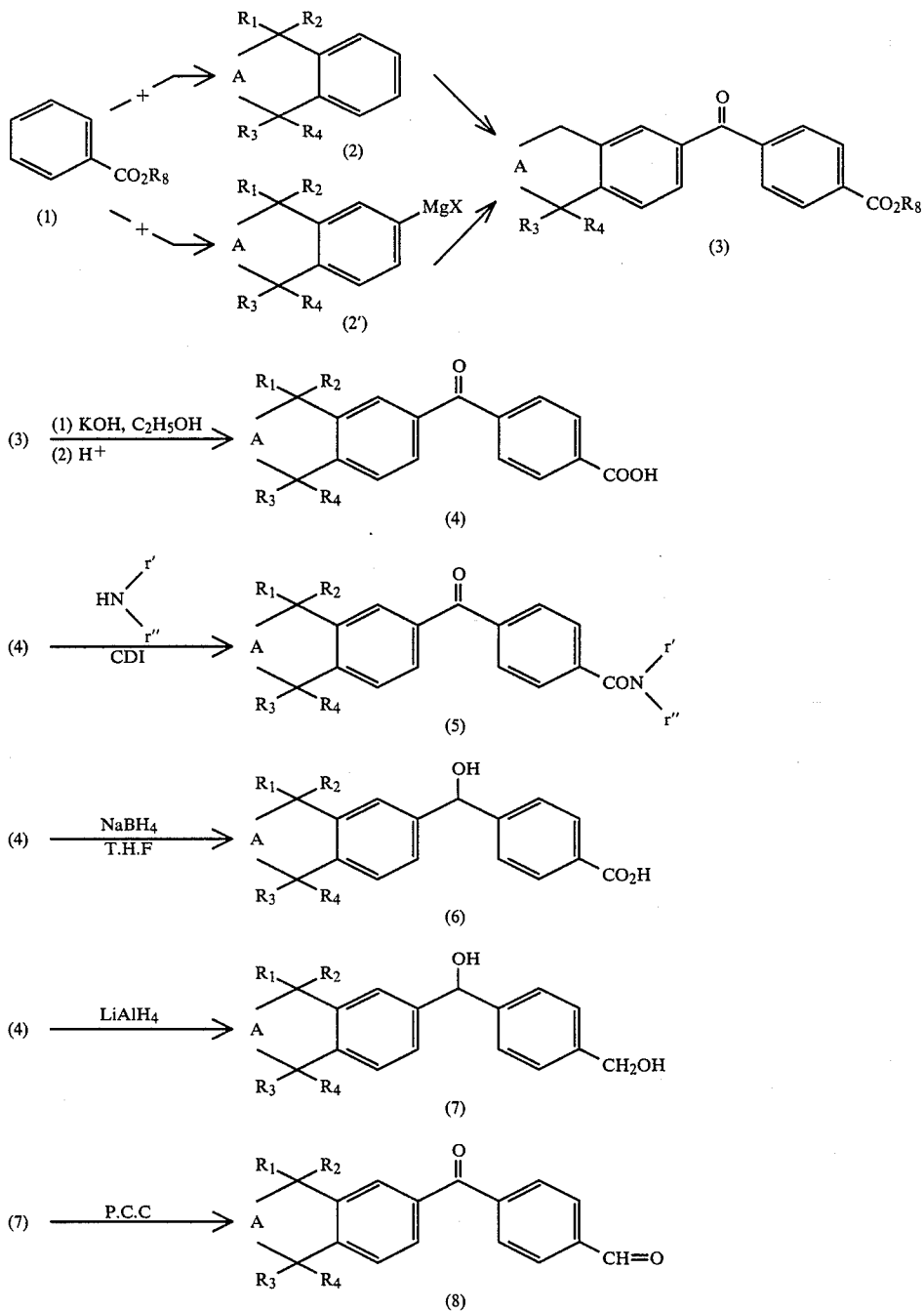

Chem. 32, 893–901 (1967). 1,1,2,3,3 pentamethylindane and 1,1,3,3 tetramethylindane are obtained by the methods described in French Pat. No. 1.392.804.

The condensation reaction of the 4-alkoxycarbonyl-2-benzoic acid chloride (1) with the bicyclic aromatic compound (2) is performed under the usual conditions of the Friedel-Crafts reaction, that is, in the presence of aluminum chloride or anhydrous stannous chloride in 1,2-dichloroethane at a temperature between 0° and 25° C., while being stirred.

The ketonic ester (3) can also be obtained by a condensation reaction of the 4-alkoxycarbonyl-2-benzoic acid chloride (1) with the magnesium salt of the aromatic halogenated derivative (2'), the latter being obtained in anhydrous THF by refluxing, and the condensation being performed at a temperature of approximately 0° C. in the same solvent.

Beginning with the ketonic ester (3), the corresponding ketonic acid (4) is obtained by saponification, which can then be converted into amide of formula (5) by action of an amine of the formula

(r' and r" having the same meaning as given above), in the presence of N,N'-carbonyl diimidazole (CDI).

When $R_8$ represents a monohydroxyalkyl or polyhydroxyalkyl radical, it is preferable to prepare the ketonic acid (4) using the methyl ester (3) ($R_8$=—$CH_3$) and then to esterify the ketonic acid thus obtained to make the ketonic ester of the selected mono- or polyhydric alcohol by known methods.

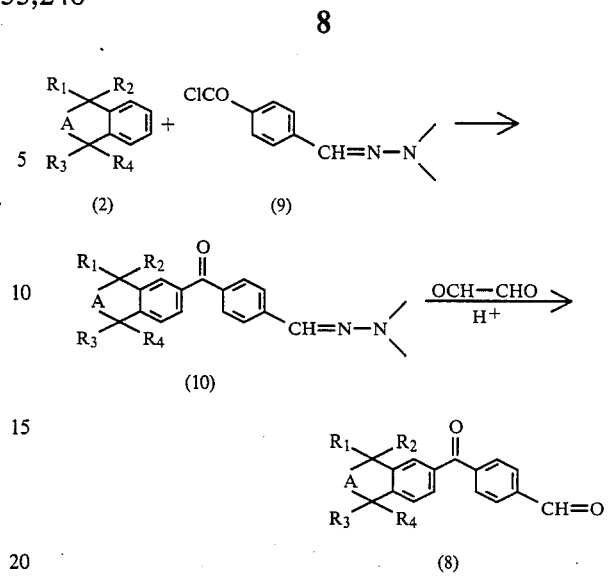

This method comprises performing a condensation reaction of the acid chloride (9), the aldehyde function of which has been protected beforehand by the formation of a dimethylhydrazone, with the bicyclic aromatic compound (1) under the same conditions as those described above for the condensation of the acid chloride (2).

The aldehyde function of the benzophenone obtained (10) is then liberated, by exchange with glyoxal, leading to a good yield of the ketonic aldehyde (8).

The ketonic aldehydes (8) are particularly useful starting materials for the synthesis of the compounds of formula III, in accordance with the following reaction scheme:

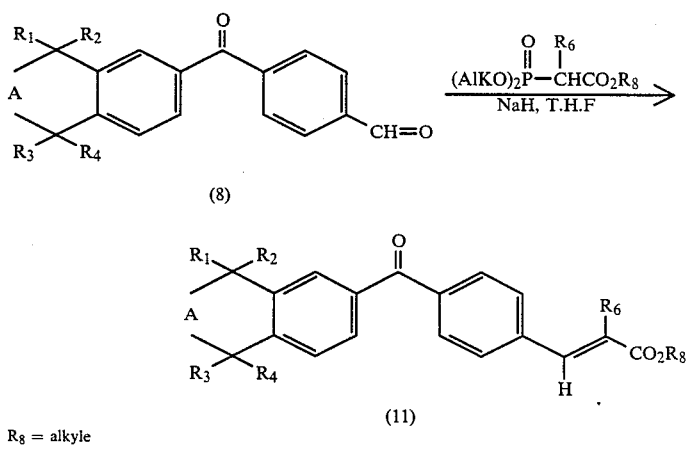

$R_8$ = alkyle

Starting with the ketonic acid (4), reduction by sodium borohydride in an organic solvent such as THF makes it possible to obtain the secondary alcohol (6), and reduction by lithium aluminum hydride of the ketonic acid (4) enables obtaining the diol (7).

By oxidation of the diol (7) by pyridinium chlorochromate (PCC), the ketonic aldehyde (8) is obtained.

The ketonic aldehyde (8), which also comprises an intermediate in the preparation of the compounds of formula III, can also be obtained in accordance with the following reaction scheme:

The Wittig-Horner reaction of the ketonic aldehyde (8) with the phosphonoacetate, substituted or not, is performed in the presence of sodium hydride in an organic solvent such as THF.

The resulting unsaturated ketonic ester (11) can then be converted as above into a corresponding acid, and then to an amide, by the action of an amine of the formula

The hydroxy acids of formula (6) and hydroxy esters (6') of the compounds of formula III can be obtained by reaction with an organic magnesium compound prepared starting with the brominated derivative (12) on an alkyl 4-formyl cinnamate (13), in accordance with the following reaction scheme:

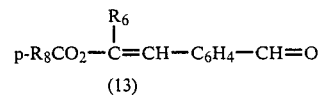

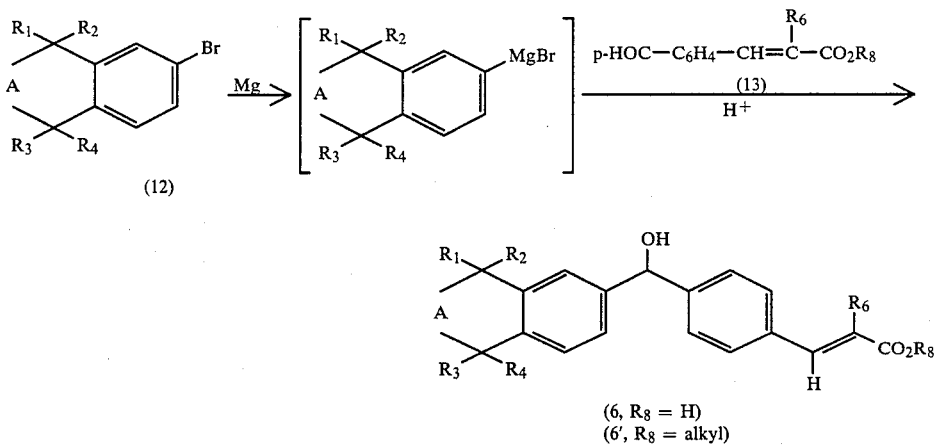

The alkyl formyl cinnamates (13) are obtained starting with commercial terephthalaldehyde (14), one of the aldehyde functions being protected in the form of dimethylhydrazone. The aldehyde (15) thus obtained is then condensed with an alkyl phosphonoacetate under the conditions of the Wittig-Horner reaction, and the protected aldehyde function is then liberated in an acidic medium by exchange with glyoxal, to obtain the alkyl formyl cinnamate (13).

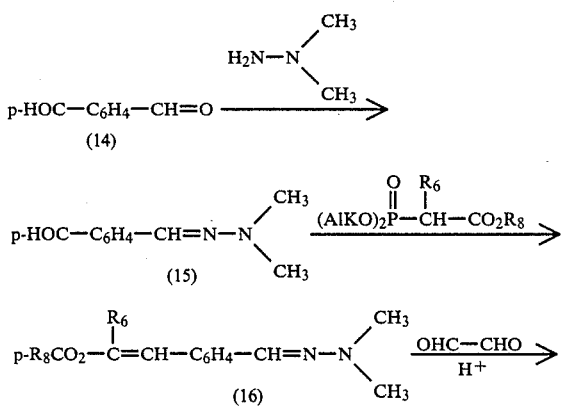

The compounds according to the invention in which $R'=R''=H$ are obtained by reduction with zinc of the ketonic derivatives in acetic acid, in the presence of hydrochloric acid.

The carbonyl reduction reactions must of course be compatible with the nature of the R group. It may perhaps be desirable to assure possible protection thereof; in any event, the carbonyl reduction does not present any problem when $R=CO_2H$.

The acyloxy derivatives of the compounds of formula I ($R'=C_1-C_4$ acyloxy, and $R''=H$) are obtained by reacting an activated form of the acid, such as an anhydride or acid chloride, with a compound according to the invention in which $R'=OH$ and $R''=H$.

The alkoxy derivatives of the compounds of formula I ($R'=C_1-C_4$ alkoxy, and $R''=H$) are also obtained starting with compounds of formula I ($R'=OH$ and $R''=H$) by known methods.

For preparing the acyloxy and alkoxy derivatives, it is preferable that the radical R is an ester, acid or amide function.

The compounds of formula I in which R' and $R''=$ methano ($CH_2=$) are obtained by the Wittig reaction in accordance with the following reaction scheme:

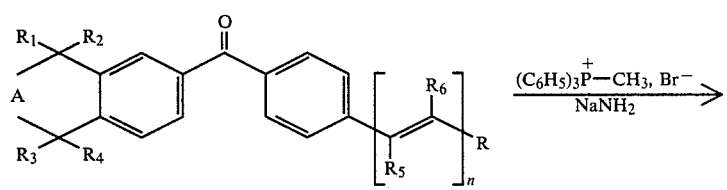

$$R \neq CHO$$

The compounds of formula I in which R′ and R″=hydroxyimino (=N—OH) are obtained by the action of hydroxylamine on the corresponding carbonyl compounds.

The present invention also relates to the compounds of formula I, as defined above, used as medications.

These compounds are active in the ornithine decarboxylase inhibition test after induction by tape stripping in nude rats (M. Bouclier et al, Dermatologica 169, No. 4 [1984]). This test is administered as a measure of antiproliferative action.

These compounds are particularly suitable for treating dermatological conditions associated with a keratinization disorder (differentiation/proliferation) as well as dermatological or other conditions having an inflammatory or immunoallergic component, in particular:

acne vulgaris, acne with comedones or polymorphous acne; senile acne, actinic acne, and medication-induced or occupational acne;

chronic and/or acute forms of psoriasis, and other keratinization problems, in particular ichthyoses and ichthyosiform conditions;

Darier's syndrome, i.e., keratosis follicularis, palmar and plantar warts;

leukoplasias and leukoplasiform conditions, lichen planus, all dermatological proliferations, whether benign or malignant, acute or chronic.

They are also active in the treatment of tumors, rheumatoid psoriasis, cutaneous or respiratory atrophies, and in certain ophthalmological problems associated with corneopathies.

These compounds also have good activity against the germs involved in acne.

Thus the compounds according to the invention exhibit good comedolytic activity in the test on the Rhino mouse described by Bonne et al, in the International Journal of Cosmetic Science 3, 23–28 (1981). These experiments are performed on the skin of hairless Rhino mice, which Van Scott recommended in 1972 as a model for screening comedolytic agents.

Accordingly, the present invention also relates to pharmaceutical compositions containing at least one compound of formula I, as defined above, or one of its salts, or one of its optical or geometric isomers.

The present invention also relates to a novel pharmaceutical composition, intended in particular for the treatment of the aforementioned conditions, characterized by the fact that it includes, in a pharmaceutically acceptable medium, at least one compound of formula I and/or one of its salts and/or one of its optical or geometric isomers.

The compounds according to the invention are generally administered in a daily dosage of approximately 2 μg/kg to 2 mg/kg of body weight.

As the medium or vehicle for the compositions, any conventional medium can be used, the active component being either in the dissolved state or dispersed in the vehicle.

Administration may be effected enterally, parenterally, topically or ocularly. For enteral administration, the medicines can be in the form of pills, gels, coated tablets, syrups, suspensions, solutions, powders, granules, or emulsions. For parenteral administration, the compositions may be in the form of solutions or suspensions for perfusion or injection.

For topical administration, the pharmaceutical compositions based on the compounds according to the invention are in the form of ointments, tinctures, creams, pomades, powders, plasters, impregnated tampons, solutions, lotions, gels, sprays, or suspensions.

These compositions for topical application can be in either anhydrous form or in an aqueous form, depending on the clinical indication.

For ocular administration, they are especially in the form of eye-washes.

The compositions for topical or ocular use preferably contain from 0.0005 to approximately 5% by weight of at least one compound of formula I, as defined above, relative to the total weight of the composition.

The compounds of formula I according to the present invention are also usable in the cosmetic field, in particular in the hygiene of the body and the hair, and especially for treating skin with acneic tendencies, for promoting hair regrowth, combatting hair loss, for counteracting the oily appearance of the skin or hair, in the prevention or treatment of the harmful effects of the sun or in the treatment of physiologically dry skin.

The present invention accordingly also relates to a cosmetic composition containing, in a cosmetically acceptable medium or vehicle, at least one compound of formula I or one of its salts and/or one of its isomers, this composition being provided in particular, in the form of a lotion, gel, cream, soap or shampoo.

The concentration of formula I compound in the cosmetic compositions ranges between 0.0005 and 2% by weight, and preferably between 0.01 and 1% by weight, based on total weight of the composition.

The pharmaceutical and cosmetic compositions according to the present invention can contain inert or even pharmacodynamically or cosmetically active additives, in particular the following: hydrating agents, such as thiamorpholinone and its derivatives or urea; antiseborrheic or antiacneic agents, such as S-carboxymethylcysteine, S-benzylcysteamine, their salts and their derivatives, tioxolone or benzoyl peroxide; antibiotics such as erythromycin and its esters, neomycin, the tetracyclines and 4,5-polymethylene-3-isothiazolones; agents promoting hair regrowth, such as "Minoxidil" (2,4-diamino-6-piperidinopyrimidine -3-oxide) and its derivatives, Diazoxide (7-chloro-3-methyl-1,2,4-benzothiadiazine-1,1-dioxide) and Phenytoin (5,5-diphenylimidazolidine-2,4-dione); anti-inflammatory steroidal and non-steroidal agents; carotenoids, and in particular β-carotene; anti-psoriasis agents such as anthraline and its derivatives and the 5,8,11,14-eicosatetraynoic and 5,8,11-triynoic acids, as well as their esters and amides; and flavor improvers, preservatives, stabilizers, moisture-regulating agents, pH-regulating agents, osmotic pressure modifiers, emulsifiers, UV-A and UV-B filters, anti-oxidants such as α-tocopherol, butylhydroxyanisole or butylhydroxytoluene.

By way of illustration, and without any limitation whatever, several examples will now be given for the preparation of the active formula I compounds according to the present invention, as well as examples of compositions containing them.

EXAMPLE 1

Preparation of methyl (5,5,8,8-tetramethyl-5,6,7,8-tetrahydro-2-naphthyl)-4-carbonyl benzoate Formula IV compound, in which $A=(CH_2)_2-$, $R'$ and $R''=oxo$ and $R'_7=-OCH_3$.

(a) Preparation of 4-methoxycarbonyl benzoic acid

To a solution of 20 g of methyl 4-formyl benzoate in 150 cm$^3$ of acetone, a solution containing 30 g of potassium bichromate in 150 cm$^3$ of water and 27 cm$^3$ of concentrated sulfuric acid is added, drop by drop. Stirring is continued for two hours at ambient temperature. After evaporation of the acetone at reduced pressure, the reaction mixture is extracted with ethyl acetate.

The organic phase is dried with magnesium sulfate and then concentrated. 11 grams of crude 4-methoxycarbonyl benzoic acid is obtained, which is recrystalized in the ethyl acetate. The crystals are filtered and dried. Melting point: 222° C. The NMR'H spectrum corresponds to the structure expected.

(b) Preparation of the 4-methoxycarbonyl benzoic acid chloride

A suspension of 5 g of the acid obtained in (a) above in 50 cm$^3$ of thionyl chloride is brought to 40° C. over the course of three hours. At the end of the reaction, the medium is homogeneous and the solution is concentrated under reduced pressure. The expected acid chloride crystallizes in the form of pink flakes. The yield of acid chloride is quantitative, and is used directly for the following step.

(c) Preparation of methyl (5,5,8,8-tetramethyl-5,6,7,8-tetrahydro-2-naphthyl)-4-carbonyl benzoate To a solution stirred at a temperature of 5° C. of 4.85 g (0.0258 mole) of 5,5,8,8-tetramethyl-5,6,7,8-tetrahydronaphthalene and 5.4 g (0.0272 mole) of the acid chloride obtained in (b) above, in 250 cm$^3$ of anhydrous 1,2-dichloroethane, 5.4 g of aluminum chloride are added in small portions. Stirring is continued for one-half hour after the end of the addition, and the reaction medium is then left overnight at ambient temperature. After being poured over ice, the organic phase is decanted, and the aqueous phase is extracted with dichloromethane.

The organic phases are combined and then washed with a saturated solution of ammonium chloride and dried with magnesium sulfate.

These solutions are concentrated and then deposited on a silica gel chromatography column. The expected product is eluted with a 9 to 1 mixture of hexane/ethyl acetate.

After evaporation of the elution phases, 3 g of a white product are obtained, which is recrystallized in hexane. The crystals are filtered and dried. The methyl (5,5,8,8-tetramethyl -5,6,7,8-tetrahydro-2-naphthyl)-4-carbonyl benzoate has a melting point of 136° C.

Elemental analysis: $C_{23}H_{26}O_3 \frac{1}{4} H_2O$: Calculated: C: 77.82; H: 7.38; O: 14.65. Found: C: 77.53; H: 7.42; O: 14.78.

EXAMPLE II

Preparation of (5,5,8,8-tetramethyl-5,6,7,8-tetrahydro-2-naphthyl)-4-carbonyl benzoic acid Formula IV compound, in which $A=-(CH_2)_2-$, $R'$ and $R''=oxo$ and $R'_7=-OH$.

A mixture of 1.5 g of the ester obtained in Example I in 100 cm$^3$ of ethanol and 100 cm$^3$ of 6N potassium is brought to 50° C. over the course of two hours while being stirred. The ethanol is then eliminated by evaporation in a vacuum. The aqueous phase obtained is then acidified by the addition of concentrated hydrochloric acid. The expected acid precipitates and is filtered and then dried and recrystallized in a hexane-toluene mixture. Thus 0.87 g of (5,5,8,8-tetramethyl-5,6,7,8-tetrahydro-2-naphthyl)-4-carbonyl benzoic acid is obtained; melting point: 193° C.

The NMR$^1$H spectrum corresponds to the expected structure.

Elemental analysis: $C_{22}H_{24}O_3$: Calculated: C: 78.54; H: 7.19; O: 14.27. Found: C: 78.50; H: 7.23; O: 14.20.

EXAMPLE III

Preparation of (5,8-methano-5,6,7,8-tetrahydro-2-naphthyl)-4-carbonyl benzaldehyde Formula II compound, in which $A=-(CH_2)_2-$, $R_1$ and $R_3=-CH_2-$, $R_2=R_4=H$, $R'$ and $R''=oxo$ and $R=-CHO$.

(a) Preparation of paraformylbenzoic acid chloride, the aldehyde function of which is protected in the form of dimethylhydrazone.

(i) Preparation of 4-formyl N,N-dimethylhydrazone benzoic acid.

To a solution, stirred at a temperature of 30° C., of 49.25 g (0.30 mole) of methyl 4-formyl benzoate in 200 cm$^3$ of anhydrous THF, 22.8 cm$^3$ of N,N-dimethylhydrazine is added drop by drop. Stirring is continued for one hour after the end of the addition, and the solvent is rectified under reduced pressure.

61.15 g of a yellow crystallized product is obtained, the NMR$^1$H spectrum of which corresponds to the expected structure.

This solid is then solubilized in a mixture of 200 cm$^3$ of ethanol and 200 cm$^3$ of 6N aqueous potash brought to 60° C.

After 1 hour and 30 minutes of agitation at this temperature, the ethanol is evaporated. The aqueous phase is diluted in 1 liter of water and the resulting solution is acidified by the addition of acetic acid. The 4-formyl N,N-dimethylhydrazone benzoic acid precipitates. It is filtered, then dried and 44.16 g of yellow crystals are obtained; melting point: 61° C. The NMR$^1$H spectrum corresponds to the expected structure.

(ii) Preparation of the acid chloride

To a suspension of 20 g (0.10 mole) of the acid obtained above, in 300 cm$^3$ of diethyloxide, 24.85 cm$^3$ of dicyclohexylamine are added, while stirring. After one hour, the dicyclohexylamine salt is filtered and then dried. 44.7 g are thus obtained of a salt having a creamy color with a melting point of 164° C. To a suspension of 11.5 g (0.0308 mole) of this salt in 250 cm$^3$ of 1,2-dichloroethane, 6 cm$^3$ of thionyl chloride are added, drop by drop. Stirring is then continued for one hour, and then the dicyclohexylammonium chloride precipitate is filtered. On evaporation of the filtrate under reduced pressure, 5.8 g of a brown powder are isolated, of which the NMR$^1$H spectrum corresponds to the expected structure. The 4-paraformyl N,N-dimethylhydrazone benzoic acid chloride is used without further purification for the next stage of the synthesis.

(b) Preparation of (5,8-methano-5,6,7,8-tetrahydro-2-naphthyl)-4-carbonyl N,N-dimethylhydrazone benzaldehyde To a mixture, stirred at a temperature lower than 5° C., of 3.1 g of benzonorbornene in 100 cm$^3$ of anhydrous 1,2-dichloroethane, 4.3 g (0.020 mole) of the acid chloride obtained above are added, and then, in small portions, 4.3 g of aluminum chloride. At the end of the addition, the mixture is again stirred for two hours and then poured over ice water. The dichloroethane phase is decanted, dried with magnesium sulfate, and evaporated under reduced pressure. The resulting product is extracted with ethyl acetate and then the organic phase is washed, using an aqueous solution of sodium bicarbonate and water.

After drying with magnesium sulfate, the ethyl acetate solution is concentrated and then deposited on a silica gel chromatography column, and the expected product is eluted with an 8 to 2 mixture of hexane and ethyl acetate. After concentration of the eluting phases, 2.6 g of (5,8-methano-5,6,7,8-tetrahydro-2-naphthyl)-4-carbonyl N,N-dimethylhydrazone benzaldehyde are obtained; melting point: 122° C.

The NMR$^1$H spectrum corresponds to the expected structure.

(c) Preparation of (5,8-methano-5,6,7,8-tetrahydro-2-naphthyl)-4-carbonyl benzaldehyde A stirred mixture of 1.85 g of hydrazone obtained above in (b), 2.8 cm$^3$ of an aqueous solution of glyoxal, 6.2M, and 5 drops of concentrated hydrochloric acid in 100 cm$^3$ of toluene is brought to a temperature of 60° C. The conversion of the hydrazone is followed by thin-film chromatography. When the starting product is completely converted, the reaction medium is washed with water, and the toluene phase is dried with magnesium sulfate. After evaporation of the toluene under reduced pressure, 1.26 g of (5,8-methano-5,6,7,8-tetrahydro-2-naphthyl)-4-carbonyl benzaldehyde are obtained, in the form of a viscous liquid, the NMR$^1$H spectrum of which corresponds to the expected structure.

EXAMPLE IV

Preparation of (5,5,8,8-tetramethyl-5,6,7,8-tetrahydro-2-naphthyl)-4-carbonyl benzaldehyde Formula IV compound, in which $A = -(CH_2)_2-$, R' and R" $=$ oxo and R'$_7$ $=$ H.

To a mixture of 14.7 g (0.078 mole) of 5,5,8,8-tetramethyl-5,6,7,8-tetrahydro-naphthalene and 16.3 g (0.077 mole) of acid chloride obtained in Example III a in 500 cm$^3$ of anhydrous 1,2-dichloroethane, 15.6 g (0.117 mole) of aluminum chloride are added, in small portions, while stirring at a temperature lower than 5° C. Stirring is continued for 30 minutes at 5° C. and then for two hours at ambient temperature, at the end of which period the reaction is stopped. The reaction mixture, which is an intense red color, is then poured over ice and the organic phase is decanted and then dried with magnesium sulfate. After evaporation of the 1,2-dichloroethane under reduced pressure, the product obtained is extracted with ethyl acetate. The organic phase is then washed with the aid of an aqueous solution of sodium bicarbonate and then with water and is then dried with magnesium sulfate.

After evaporation of the ethyl acetate under reduced pressure and ensuing purification by silica gel chromatography, 9.25 g of (5,5,8,8-tetramethyl-5,6,7,8-tetrahydro-2-naphthyl)-4-carbonyl N,N-dimethylhydrazone benzaldehyde are obtained in the form of crystals having a melting point of 119° C.

To a solution of 6.8 g of the resulting hydrazone in 250 cm$^3$ of toluene, 13.5 cm$^3$ of an aqueous solution of glyoxal, 6.2M, and 2 cm$^3$ of concentrated hydrochloric acid are added. The mixture is then brought to 60° C. over the course of 4 hours and then brought to ambient temperature and washed with 200 cm$^3$ of water. The toluene phase is then decanted, dried with magnesium sulfate and then concentrated at reduced pressure.

5.5 g of (5,5,8,8-tetramethyl-5,6,7,8-tetrahydro-2-naphthyl)-4-carbonyl benzaldehyde are obtained, in the form of a yellow powder having a melting point of 127°–130° C.

The NMR$^1$H spectrum corresponds to the expected structure.

EXAMPLE V

Synthesis of methyl (1,1,2,3,3-pentamethyl-5-indanyl)-4-carbonyl benzoate

Formula IV compound, in which $A = CH_3-CH<$, R' and R" $=$ oxo and R'$_7$ $=$ $-OCH_3$.

To a suspension stirred at ambient temperature, of 5 g (0.027 mole) of 1,1,2,3,3-pentamethyl indane and 5 g (0.025 mole) of methoxy-4-carbonyl benzoic acid chloride in 100 cm$^3$ of anhydrous 1,2-dichloroethane, 6 g of powdered aluminum chloride are added in small portions in such a way as to keep the temperature below 35° C.

Stirring is continued for one hour, until the total disappearance of the starting product, and then the reaction mixture is poured over 150 cm$^3$ of ice water and extracted with dichloromethane.

The organic phase is washed with an aqueous solution of sodium bicarbonate, and then with water, dried with magnesium sulfate and concentrated at reduced pressure.

On purification with silica gel chromatography (eluant-9 to 1 mixture of hexane/ethyl acetate), 6.5 g of methyl (1,1,2,3,3-pentamethyl-5-indanyl)-4-carbonyl benzoate are obtained; melting point: 146°–147° C. (after recrystallization in the hexane).

Elemental analysis: $C_{23}H_{26}O_3$: Calculated: C: 78.82; H: 7.48; O: 13.70. Found: C: 78.74; H: 7.52; O: 13.80.

EXAMPLE VI

Synthesis of (1,1,2,3,3-pentamethyl-5-indanyl)-4-carbonyl benzoic acid

Compound of formula IV, in which $A = CH_3-CH<$, R' and R" $=$ oxo and R'$_7$ $=$ OH.

A suspension of 4.9 g of methyl (1,1,2,3,3-pentamethyl-5-indanyl)-4-carbonyl benzoate obtained in Example V in 200 cm$^3$ of ethyl alcohol and 75 cm$^3$ of a 6N aqueous solution of potash is brought to 40° C. over approximately 3 hours, until the total disappearance of the starting product. After evaporation of the alcohol under reduced pressure, the aqueous phase is diluted with 500 cm$^3$ of water, cooled to 0° C. and acidifed with concentrated hydrochloric acid. The precipitate obtained is filtered, dried and recrystallized in a hexane-toluene mixture. 3.9 g of a white powder having a melting point of 164°–165° C. are thus obtained.

The NMR$^1$H spectrum agrees with the structure of (1,1,2,3,3-pentamethyl-5-indanyl)-4-carbonyl benzoic acid.

Elemental analysis: $C_{22}H_{24}O_3$: Calculated: C: 78.54; H: 7.19; O: 14.57. Found: C: 78.40; H: 7.23; O: 14.21.

EXAMPLE VII

Synthesis of N-ethyl (1,1,2,3,3-pentamethyl-5-indanyl)-2-carbonyl benzamide

Formula IV compound, in which A=CH$_3$—CH<, R' and R"=oxo and R'$_7$=—NHC$_2$H$_5$.

To a solution of 2.5 g of (1,1,2,3,3-pentamethyl-5-indanyl)-4-carbonyl benzoic acid obtained in Example VI, in 100 cm$^3$ of anhydrous dichloromethane, 2.5 g of N,N'-carbonyldiimidazole are added. After the addition, stirring is continued for 3 hours, and then the reaction mixture is cooled to 0° C. and 2.5 cm$^3$ of anhydrous ethylamine are added. Stirring is continued for 2 hours at ambient temperature and then the solution is poured over 200 cm$^3$ of water. The aqueous phase is extracted with dichloromethane and the organic phases are combined, washed, dried with magnesium sulfate and concentrated under reduced pressure.

The oil thus obtained crystallizes in diisopropyl ether to yield 1.9 g of N-ethyl (1,1,2,3,3-pentamethyl-5-indanyl)-2-carbonyl benzamide; melting point: 132°–133° C.

Elemental analysis: $C_{24}H_{29}NO_2$: Calculated: C: 79.30; H: 8.04; N: 3.85; O: 8.80. Found: C: 79.08; H: 8.06; N: 3.92; O: 8.74.

EXAMPLE VIII

Synthesis of 1-(1,1,2,3,3-pentamethyl-5-indanyl)-1-(4-hydroxymethylphenyl) methanol Compound of Formula II, in which A=CH$_3$—CH<, R$_1$=R$_2$=R$_3$=R$_4$=CH$_3$; R'=OH, R"=H and R=—CH$_2$OH.

To a suspension of 3.3 g of aluminum lithium hydride in 200 cm$^3$ of anhydrous tetrahydrofurane maintained at 0° C., a solution of 10 g of (1,1,2,3,3-pentamethyl-5-indanyl)-4-carbonyl methyl benzoate obtained in Example V, in 100 cm$^3$ of tetrahydrofurane, is added, drop by drop. After the end of the addition, stirring of the reaction mixture is continued at ambient temperature for approximately 3 hours, until the total disappearance of the starting product and of the intermediate reduction products. After addition of 50 cm$^3$ of ethyl acetate to destroy the excess hydride, the solution is poured over 200 cm$^3$ of water, acidified with 3N hydrochloric acid and extracted with ethyl acetate. The organic phases are washed, dried with magnesium sulfate and concentrated under reduced pressure. The yield is 4.1 g of (1,1,2,3,3-pentamethyl-5-indanyl)-1-(4-hydroxymethylphenyl) methanol, which crystallizes in the hexane in the form of a white powder having a melting point of 107°–108° C.; the NMR$^1$H 80 MHz spectrum of which conforms to the expected structure.

EXAMPLE IX

Synthesis of (1,1,2,3,3-pentamethyl-5-indanyl)-4-carbonyl benzaldehyde

Compound of Formula IV, in which A=CH$_3$—CH<, R' and R"=oxo and R'$_7$=H.

To a solution of 2 g (0.0062 mole) of (1,1,2,3,3-pentamethyl-5-indanyl)-1-(4-hydroxymethylphenyl) obtained in Example VIII, in 100 cm$^3$ of anhydrous dichloromethane, 3.4 g of pyridinium chlorochromate are added.

Stirring is continued for approximately 3 hours, until the total disappearance of the starting product, and then, after addition of 200 cm$^3$ of dichloromethane and approximately 20 g of silica, the solution is filtered, washed with a solution of ammonium chloride and water, and then dried with magnesium sulfate and concentrated at reduced pressure. After crystallization in a mixture of hexane and diisopropyl ether, 1.2 g of a white powder are obtained, melting point: 114°–115° C., the NMR$^1$H 80 MHz spectrum of which conforms to the expected structure.

Elemental analysis: $C_{22}H_{24}O_2$; Calculated: C: 82.46; H: 7.55; O: 9.99. Found: C: 82.31; H: 7.56; O: 10.02.

EXAMPLE X

Synthesis of methyl (1,1,2,3,3-pentamethyl-5-indanyl)-4-hydroxymethyl benzoate Compound of Formula IV, in which A=CH$_3$—CH<, R'=OH and R"=H, and R'$_7$=—OCH$_3$.

To a suspension of 2 g of methyl (1,1,2,3,3-pentamethyl-5-indanyl)-4-carbonyl benzoate obtained in Example V, in 100 cm$^3$ of methanol, 0.7 g of sodium borohydride is added in small portions, while keeping the temperature below 30° C. Stirring is continued at ambient temperature for approximately 3 hours, until the total disappearance of the starting product. The reaction mixture is hydrolyzed with 100 cm$^3$ of water and acidified with a solution of 3N hydrochloric acid. After evaporation of the methanol under reduced pressure, the expected product is extracted with ethyl acetate. The organic phases are washed, dried and concentrated under reduced pressure. The yield is 1.7 g of a white powder, the NMR$^1$H spectrum of which corresponds to the structure of methyl (1,1,2,3,3-pentamethyl-5-indanyl)-4-hydroxymethyl benzoate. On recrystallization of a sample in hexane, white flakes are obtained, having a melting point of 126°–127° C.

Elemental analysis: $C_{23}H_{28}O_3$; Calculated: C: 78.37; H: 8.00; O: 13.62. Found: C: 78.33; H: 7.93; O: 13.71.

EXAMPLE XI

Synthesis of (1,1,2,3,3-pentamethyl-5-indanyl)-4-hydroxymethyl benzoic acid

Compound of Formula IV, in which A=CH$_3$—CH<, R'=OH and R"=H, and R'$_7$—OH.

A suspension of 1 g of methyl (1,1,2,3,3-pentamethyl-5-indanyl)-4-hydroxymethyl benzoate obtained in Example X, in a mixture of 100 cm$^3$ of ethyl alcohol and 30 cm$^3$ of a 6N aqueous solution of potash, is heated to 40° C. for approximately 1 hour, until the total disappearance of the starting product. The alcohol is evaporated under reduced pressure, and then the aqueous phase is diluted with 300 cm³ of water. After being cooled to 0° C. and acidified with 3N hydrochloric acid, the resulting precipitate is filtered, dried and recrystallized in a hexane-toluene mixture. 600 mg of a white powder are recovered; melting point: 187°–188° C.

The NMR¹H 80 MHz spectrum conforms to the structure of (1,1,2,3,3-pentamethyl-5-indanyl)-4-hydroxymethyl benzoic acid.

Elemental analysis: $C_{22}H_{26}O_3$; Calculated: C: 78.07; H: 7.74; O: 14.18. Found: C: 77.87; H: 7.67; O: 14.31.

EXAMPLE XII (5,5,8,8-tetramethyl-5,6,7,8-tetrahydro-2-naphthyl)-4-hydroxymethyl-4 benzoic acid.

Compound of Formula IV, in which $A=(CH_2)_2$, $R'=OH$, $R''=H$, and $R'_7=-OH$.

To a solution, stirred at ambient temperature, of 0.5 g of (5,5,8,8-tetramethyl-5,6,7,8-tetrahydro-2-naphthyl)-4-carbonyl benzoic acid, obtained in Example II, in 50 cm³ of methanol, 0.25 g of sodium borohydride is added drop by drop, in small portions. Stirring is continued for approximately 1 hour, until the total disappearance of the starting product. The reaction mixture is then hydrolyzed with 100 cm³ of water and then acidified with concentrated hydrochloric acid.

After evaporation at reduced pressure of the methanol, the aqueous phase is diluted with 50 cm³ of water and extracted with ethyl acetate. The organic phases are washed, dried with magnesium sulfate and concentrated at reduced pressure. On recrystallization in a mixture of hexane and toluene, 200 mg of a white powder are obtained, having a melting point of 177°–178° C. The NMR¹H 80 MHz spectrum corresponds to the structure of (5,5,8,8-tetramethyl-5,6,7,8-tetrahydro-2-naphthyl)-4-hydroxymethyl-4 benzoic acid.

Elemental analysis: $C_{22}H_{26}O_3$; Calculated: C: 78.07; H: 7.74; O: 14.18. Found: C: 78.00; H: 7.76; O: 14.23.

EXAMPLE XIII

Preparation of ethyl trans-(5,8-methano-5,6,7,8-tetrahydro-2-naphthyl)-4-carbonyl cinnamate Compound of Formula III, in which $A=(CH_2)_2$, $R_1$ and $R_3=CH_2-$, $R_2=R_4=R_5=R_6=H$, $R'$ and $R''=oxo$ and $R=CO_2C_2H_5$ To a solution, stirred at ambient temperature, of 1.83 cm³ (9 mmoles) of triethylphosphonoacetate in 75 cm³ of anhydrous THF, 0.45 g of sodium hydride is added in small fractions. Then, in the absence of light, a solution of 1.7 g (6 mmoles) of (5,8-methano-5,6,7,8-tetrahydro-2-naphthyl)-4-carbonyl benzaldehyde, obtained in Example III, in 10 cm³ of THF is added. The development of the reaction is followed by thin-film chromatography. At the end of the reaction, the mixture is poured over ice and then extracted three times with 100 cm³ of ethyl acetate. The organic phases are combined, washed with a saturated solution of ammonium chloride and then with water and finally dried with magnesium sulfate. The ethyl acetate is rectified under reduced pressure and the expected product is crystallized by stirring in hexane.

1.5 g of ethyl trans-(5,8-methano-5,6,7,8-tetrahydro-2-naphthyl)-4-carbonyl cinnamate are thus obtained, in the form of white crystals having a melting point of 92° C.

The NMR¹H corresponds to the expected structure.

EXAMPLE XIV

Preparation of (5,8-methano-5,6,7,8-tetrahydro-2-naphthyl)-4-carbonyl cinnamic acid Compound of Formula III, in which $A=-(CH_2)_2-$, $R_1$ and $R_3=-CH_2-$, $R_2=R_4=R_5=R_6=H$, $R'$ and $R''=oxo$ and $R=-CO_2H$.

A stirred suspension, in the absence of light, of 1.3 g of ethyl trans-(5,8-methano-5,6,7,8-tetrahydro-2-naphthyl)-4-carbonyl cinnamate obtained in Example XIII, in 50 cm³ of ethanol and 50 cm³ of a 6N aqueous solution of potash is brought to a temperature of 50° C. for approximately one hour. After evaporation of the ethanol under reduced pressure, the aqueous phase is acidified at ambient temperature, while being stirred, with the addition of hydrochloric acid. The precipitate formed is then filtered, dried and then recrystallized in a hexanetoluene mixture. 0.750 g of (5,8-methano-5,6,7,8-tetrahydro -2-naphthyl)-4-carbonyl cinnamic acid is obtained in the form of white crystals having a melting point of 189° C.

The NMR¹ corresponds to the expected structure.

Elemental analysis: $C_{21}H_{18}O_3$; Calculated: C: 79.22; H: 5.70; O: 15.08. Found: C: 79.20; H: 5.75; O: 15.11.

EXAMPLE XV

Preparation of ethyl trans-(5,5,8,8-tetramethyl-5,6,7,8-tetrahydro-2-naphthyl)-4-carbonyl cinnamate Compound of Formula V, in which $A=-(CH_2)_2-$, $R_6=H$, $R'$ and $R''=oxo$ and $R'_7=-OC_2H_5$.

To a solution of 4.8 cm³ (24.3 mmoles) of triethylphosphonoacetate in 150 cm³ of anhydrous THF, 1.17 g (24 mmoles) of sodium hydride are added in small fractions. To this mixture, stirred at ambient temperature and in the absence of light, a solution of 5.2 g (16.2 mmoles) of (5,5,8,8-tetramethyl-5,6,7,8-tetrahydro-2-naphthyl)-4-carbonyl benzaldehyde obtained in Example IV, in 50 cm³ of anhydrous THF, is introduced drop by drop. Stirring is continued in the absence of light until the complete conversion of the starting product. The reaction medium is then poured over an aqueous solution of ammonium chloride and the mixture is extracted with ethyl acetate. The organic phase is decanted, washed with water and dried with magnesium sulfate.

It is then filtered and recrystallized in a hexane-toluene mixture.

3 g of ethyl trans-(5,5,8,8-tetramethyl-5,6,7,8-tetrahydro-2-naphthyl)-4-carbonyl cinnamate are isolated, in the form of white crystals having a melting point of 97° C. By passage of the filtrate through a silica gel chromatography column and elution of the expected product with a mixture of hexane and ethyl acetate, 1 g of the pure supplementary product is obtained.

Elemental analysis: $C_{26}H_{40}O_3$; Calculated: C: 79.96; H: 7.74; O: 12.29. Found: C: 80.01; H: 7.77; O: 12.20.

EXAMPLE XVI

Preparation of trans-(5,5,8,8-tetramethyl-5,6,7,8-tetrahydro-2-naphthyl)-4-carbonyl cinnamic acid Compound of Formula V, in which $A=-(CH_2)_2-$, $R_6=H$, $R'$ and $R''=oxo$ and $R'_7=OH$.

A suspension of 3 g of ethyl trans-(5,5,8,8-tetramethyl-5,6,7,8-tetrahydro-2-naphthyl)-4-carbonyl cinnamate obtained in Example XV in a mixture of 100 cm$^3$ of ethanol and 100 cm$^3$ of 6N aqueous potash is stirred at 50° C., in the absence of light, for two hours. The ethanol is then eliminated by evaporation under a vacuum, and the residual aqueous phase is acidified by the addition of concentrated hydrochloric acid. After 30 minutes of stirring, the resulting precipitate is filtered, dried, and then dissolved in a minimum of methylene chloride and deposited on a silica gel chromatography column. The expected product is eluted with a 1:1 mixture of hexane and dichloromethane.

After evaporation of the eluant, trans-(5,5,8,8tetramethyl -5,6,7,8-tetrahydro-2-naphthyl)-4-carbonyl cinnamic acid is obtained, in the form of white crystals; melting point: 232° C.

Elemental analysis: $C_{24}H_{26}O_3$; Calculated: C: 79.53; H: 7.23; O: 13.24. Found: C: 79.29; H: 7.21; O: 13.05.

EXAMPLE XVII

Preparation of ethyl trans-(5,5,8,8-tetramethyl-5,6,7,8-tetrahvdro-2-naphthyl)-4-carbonyl-α-methyl cinnamate Compound of formula V, in which: $A=-(CH_2)_2-$, $R_6=-CH_3$, R' and R"=oxo and $R'_7=-OC_2H_5$.

To a solution of 1.95 g (8.2 mmoles) of 2-triethylphosphonopropionate, in 100 cm$^3$ of anhydrous THF, 0.44 g (9 mmoles) of sodium hydride is added in small portions with stirring. After 30 minutes, in the absence of light, a solution of 1.75 g (5.5 mmoles) of (5,5,8,8-tetramethyl-5,6,7,8-tetrahydro-2-naphthyl)-4-carbonyl benzaldehyde obtained in Example IV, in 20 cm$^3$ of THF, is added.

After 3 hours of stirring, the reaction mixture is poured over ice water and the resulting solution is extracted three times with the aid of 50 cm$^3$ of ethyl acetate. The organic phases are combined, washed with 100 cm$^3$ of water, dried with magnesium sulfate and concentrated under reduced pressure. The expected product is purified by passage over a silica gel column by elution with a 95 to 5 mixture of hexane and ethyl acetate. After evaporation of the eluant under reduced pressure, ethyl trans-(5,5,8,8-tetramethyl-5,6,7,8-tetrahydro-2-naphthyl)-4-carbonyl-α-methyl cinnamate is isolated in the form of white crystals having a melting point of 106° C.

Elemental analysis: $C_{27}H_{32}O_3$; Calculated: C: 80.16; H: 7.97; O: 11.87. Found: C: 80.24; H: 7.98; O: 11.68.

EXAMPLE XVIII

Preparation of trans-(5,5,8,8-tetramethyl-5,6,7,8-tetrahydro-2-naphthyl)-4-carbonyl-α-methyl cinnamic acid Compound of formula V, in which: $A=-(CH_2)_2-$, $R_6=-CH_3$, R' and R"=oxo and $R'_7=-OH$.

A suspension of 2.75 g of ethyl trans-(5,5,8,8-tetramethyl-5,6,7,8-tetrahydro-2-naphthyl)-4-carbonyl-α-methyl cinnamate obtained in Example XVII is stirred for two hours in a mixture of 100 cm$^3$ of ethanol and 25 cm$^3$ of 6N aqueous potash at approximately 40° C. After evaporation of the ethanol under reduced pressure, the residue is taken up in 200 cm$^3$ of water and acidified with concentrated hydrochloric acid. On recrystallization in a toluene-hexane mixture, 1.9 g of trans-(5,5,8,8-tetramethyl-5,6,7,8-tetrahydro-2-naphthyl)-4-carbonyl-α-methyl cinnamic acid are obtained; melting point: 205°-206° C.

Elemental analysis: $C_{25}H_{28}O_3$; Calculated: C: 79.75; H: 7.50; O: 12.75. Found: C: 79.25; H: 7.52; O: 12.39.

EXAMPLE XIX

Preparation of ethyl (1,1,2,3,3-pentamethyl-5-indanyl)-4-carbonyl-α-methyl cinnamate Compound of formula V, in which: $A=CH_3-CH<$, $R_6=-CH_3$, R' and R"=oxo and $R'_7=-OC_2H_5$.

To a solution of 1.5 cm$^3$ of triethyl-2-phosphonopropionate in 100 cm$^3$ of anhydrous THF, 0.4 g of sodium hydride is added in small portions. Stirring is continued for approximately 1 hour, and then in the absence of light, a few drops of ring ether and a solution of 1.4 g of (1,1,2,3,3-pentamethyl-5-indanyl)-4-carbonyl benzaldehyde obtained in Example IX in solution in 25 cm$^3$ of anhydrous tetrahydrofurane are added. At the end of the addition, stirring is continued for 2 hours, and then the reaction medium is poured over a saturated solution of ammonium chloride and extracted with ethyl acetate.

The organic phases are washed, dried and concentrated at reduced pressure. On crystallization in hexane, 1.1 g of ethyl (1,1,2,3,3-pentamethyl-5-indanyl)-4-carbonyl-a-methyl cinnamate are recovered, in the form of a white powder having a melting point of 89°-90° C., of which the NMR$^1$H 80 MHz spectrum conforms to the expected structure.

Elemental analysis: $C_{27}H_{32}O_3$; Calculated: C: 80.16; H: 7.97; O: 11.87. Found: C: 79.70; H: 8.08; O: 11.75.

EXAMPLE XX

Preparation of trans-(1,1,2,3,3-pentamethyl-5-indanyl)-4-carbonyl-α-methyl cinnamic acid Compound of formula V, in which: $A=CH_3-CH<$, $R_6=-CH_3$, R' and R"=oxo and $R'_7=-OH$.

A suspension of 0.9 g of ethyl (1,1,2,3,3-pentamethyl-5-indanyl)-4-carbonyl-α-methyl cinnamate obtained in Example XIX is stirred for approximately 1 hour in a mixture of 100 cm$^3$ of ethanol and 30 cm$^3$ of 6N aqueous potash, at a temperature between 40° and 50° C. After evaporation of the ethanol at reduced pressure, the residue is taken up in 500 cm$^3$ of water and acidified with 3N hydrochloric acid. The expected acid precipitates. It is filtered, washed and dried.

On recrystallization in a mixture of toluene and hexane, 600 mg of a white powder, having a melting point of 171°-172° C., are recovered, the NMR$^1$H 80 MHz spectrum of which corresponds to the structure of trans-(1,1,2,3,3-pentamethyl-5-indanyl)-4-carbonyl-α-methyl cinnamic acid.

Elemental analysis: $C_{25}H_{28}O_3$;
Calculated: C: 79.15; H: 7.50; O: 12.75.
Found: C: 79.10; H: 7.54; O: 12.60.

EXAMPLE XXI

Preparation of ethyl trans-(5,5,8,8-tetramethyl-5,6,7,8-tetrahydro-2-naphthyl)-4-hydroxymethyl cinnamate Compound of formula V, in which: $A=-(CH_2)_2-$, $R_6=H$, $R'=OH$, $R"=H$ and $R'_7=-OC_2H_5$.

(1) Preparation of ethyl 4-formyl cinnamate
(a) mono-N,N-dimethylhydrazino terephthalaldehyde To a solution of 75 g of terephthalaldehyde in 800 cm³ of anhydrous THF, a solution of 42 cm³ of N,N-dimethyl hydrazine in 50 cm³ of THF is added drop by drop in such a manner as to maintain the temperature of the reaction medium below 30° C. At the end of the addition, the stirring is continued for 2 hours, until the total disappearance of the starting terephthalaldehyde. After evaporation of the THF and crystallization of the product in heptane, 93 g of mono-N,N-dimethylhydrazinoterephthalaldehyde are recovered, containing a small portion of di-N,N-dimethylhydrazinoterephthaldehyde. The product obtained is used as such for the ensuing reaction.

(b) ethyl (N,N-dimethylhydrazino)-4-formyl cinnamate

To a solution of 23 cm³ of triethylphosphonoacetate in 400 cm³ of THF, 6 g of sodium hydride are added in small portions.

At the end of the addition, stirring is continued for 2 hours, and then in the absence of light, 10 g of mono-N,N-dimethylhydrazinoterephthalaldehyde obtained above are added, in solution in 100 cm³ of THF, in such a manner that the temperature is kept below 30° C. At the end of the addition, stirring is continued for approximately 1 hour, until the total disappearance of the starting aldehyde. The reaction mixture is poured over a solution of ammonium chloride and extracted with ethyl acetate. The organic phases are washed, dried with magnesium sulfate and concentrated at reduced pressure. 10 g of an oil are recovered, the NMR¹H 80 MHz spectrum of which corresponds to the expected structure and is used in its crude form for the following reaction.

(c) ethyl 4-formyl cinnamate

To a solution of 10 g of ethyl N,N-dimethylhydrazino-4-formyl cinnamate obtained above, in 150 cm³ of toluene, 28 cm³ of aqueous glyoxal (6.2 M) and approximately 1 cm³ of concentrated hydrochloric acid are added. The solution is brought to 70° C. for approximately 2 hours until the disappearance of the starting product. The organic phase is decanted, washed with water, dried with magnesium sulfate and concentrated under reduced pressure.

After purification by silica gel chromatography (eluant: 8 to 2 hexane and ethyl acetate), 4 g of ethyl 4-formyl cinnamate are obtained in the form of an oil, the NMR¹H 80 MHz spectrum of which corresponds to the expected structure.

(2) Preparation of ethyl trans-(5,5,8,8-tetramethyl-5,6,7,8-tetrahydro-2-naphthyl)-4-hydroxymethyl cinnamate.

A solution of 5.2 g (0.0195 mole) of 5,5,8,8-tetramethyl-5,6,7,8-tetrahydro-2-bromonaphthalene in 50 cm³ of anhydrous THF is added to 550 mg of magnesium while maintaining reflux until the disappearance of the magnesium. The reaction mixture is then cooled to 0° C. and a solution of 1.9 g of ethyl 4-formyl cinnamate, obtained above, in 20 cm³ of THF is added, drop by drop. At the end of the addition the reaction mixture is stirred for 1 hour and 30 minutes at ambient temperature. The reaction mixture is poured over 200 cm³ of a solution of ammonium chloride and then extracted with ether. The organic phase is washed, dried with magnesium sulfate and then concentrated under reduced pressure. The expected product is purified by silica gel chromatography (eluant: 9 to 1 mixture of heptane and ethyl acetate) and 1.1 g of an oil are recovered, the NMR¹H 80 MHz spectrum of which corresponds to the structure of ethyl trans-(5,5,8,8-tetramethyl-5,6,7,8-tetrahydro-2-naphthyl)-4-hydroxymethyl cinnamate.

EXAMPLE XXII

Preparation of trans-(5,5,8,8-tetramethyl-5,6,7,8-tetrahydro-2-naphthyl)-4-hydroxymethyl cinnamic acid Compound of formula V, in which: $A=-(CH_2)_2-$, $R_6=H$, $R'=OH$, $R''=H$ and $R'_7=-OH$.

A solution of 1.1 g of ethyl trans-(5,5,8,8-tetramethyl-5,6,7,8-tetrahydro-2-naphthyl)-4-hydroxymethyl cinnamate obtained in Example XXI is heated to 40° C. in a mixture of 100 cm³ of ethyl alcohol and 75 cm³ of 6N aqueous potash until the disappearance of the starting product. The ethanol is evaporated under reduced pressure, and the residue is taken up in 300 cm³ of water. The mixture is cooled to 0° C. and acidified with a solution of 3N hydrochloric acid. The expected product is filtered, washed and dried.

On recrystallization in a toluene-hexane mixture, 800 mg of trans-(5,5,8,8-tetramethyl-5,6,7,8-tetrahydro-2-naphthyl)-4-hydroxymethyl cinnamic acid are obtained; melting point: 199°–200° C.

Elemental analysis: $C_{24}H_{28}O_3$; Calculated: C: 79.09; H: 7.74; O: 13.17. Found: C: 79.09; H: 7.67; O: 12.98.

EXAMPLE XXIII

Preparation of 4'-(2-hydroxyethyl)piperazino(5,5,8,8-tetramethyl-5,6,7,8-tetrahydro-2-naphthyl) 4-carbonyl benzamide Compound of formula IV, in which: $A=-(CH_2)_2-$, R' and R''=oxo and $R'_7=$

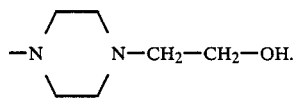

To a solution of 3 g of (5,5,8,8-tetramethyl-5,6,7,8-tetrahydro-2-naphthyl)-4-carbonyl benzoic acid from Example II in 150 cm³ of anhydrous dichloromethane, 2.9 g of N,N'-carbonyldiimidazole are added. After addition, stirring is continued for 3 hours, and then 1.75 g of 2-hydroxyethyl piperazine are added, drop by drop, and stirring is again continued for 2 hours, until the disappearance in CCM of the starting acid. The reaction mixture is poured over 200 cm³ of water, extracted with 3 x 100 cm³ of dichloromethane. The organic phases are combined, washed, dried with magnesium sulfate and concentrated under reduced pressure. On purification with silica gel (eluant: 8 to 2 ethyl acetate and methanol), 2.2 g of 4'-(2-hydroxyethyl)piperazino(5,5,8,8-tetramethyl-5,6,7,8-tetrahydro-2-naphthyl) 4-carbonyl benzamide is recovered, which crystallizes in a toluene-hexane mixture and has a melting point of 118° C.

Elemental analysis: $C_{28}H_{36}N_2O_3$; Calculated: C: 74.96; H: 8.09; N: 6.25; O: 10.70. Found: C: 74.47; H: 8.17; N: 6.21; O: 11.07.

EXAMPLE XXIV

Preparation of N-(3.5-di-trifluoromethyl-1-phenyl)-(5,5,8,8-tetramethyl-5,6,7,8-tetrahydro-2-naphthyl)-4-carbonyl benzamide Compound of formula IV, in which: $A=-(CH_2)_2-$, R' and R''=oxo and $R'_7=$

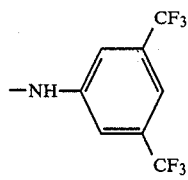

To a suspension of 1 g of (5,5,8,8-tetramethyl-5,6,7,8-tetrahydro-2-naphthyl)-4-carbonyl benzoic acid from Example II, in 75 cm³ of anhydrous diethyloxide, 0.8 cm³ of dicyclohexamine, in solution in 10 cm³ of diethyloxide, is added, drop by drop. Stirring is continued for 2 hours, and then the precipitate obtained is filtered. 1.5 g of a white powder is obtained, which is put into solution in 75 cm³ of anhydrous 1,2-dichloroethane. A solution of 0.3 cm³ of thionyl chloride in 10 cm³ of 1,2-dichloroethane is added, drop by drop. At the end of the addition, stirring is continued overnight at ambient temperature. The reaction mixture is filtered and concentrated under reduced pressure. Approximately 1 g of a yellow oil is recovered, which corresponds to (5,5,8,8-tetramethyl-5,6,7,8-tetrahydro-2-naphthyl)-4-carbonyl benzoic acid chloride.

To a solution of 1 g of the acid chloride obtained above, in 75 cm³ of 1,2-dichloroethane, a solution of 0.7 g of bis-3,5-trifluoromethylaniline in 10 cm³ of dichloromethane is added drop by drop. At the end of the addition, the reaction medium is stirred for 2 hours and then poured over 200 cm³ of water and extracted with dichloromethane. The organic phase is washed with a solution of sodium bicarbonate and then with water, dried with magnesium sulfate and concentrated under reduced pressure. The residue is taken up in hexane and filtered. 1.2 g of N-(3,5-ditrifluoromethyl-1-phenyl)-(5,5,8,8-tetramethyl-5,6,2,8-tetrahydro-2-naphthyl)-4-carbonyl benzamide are recovered, the NMR¹H 80 MHz spectrum of which conforms to the expected structure and the melting point of which is 215°–216° C.

Elemental analysis: $C_{30}H_{27}F_6NO_2$; Calculated: C: 65.80; H: 4.97; F: 20.82; N: 2.56. Found: C: 66.02; H: 4.93; F: 20.85; N: 2.48.

EXAMPLE XXV

Preparation of N-ethyl-trans-(5,5,8,8-tetramethyl-5,6,7,8-tetrahydro-2-naphthyl)-4-carbonyl-α-methyl cinnamide Compound of formula V, in which: $A=-(CH_2)_2-$, $R_6=-(CH_3)$, R' and R"=oxo and $R'_7=-NHC_2H_5$.

To a stirred solution of 3 g of trans-(5,5,8,8-tetramethyl-5,6,7,8-tetrahydro-2-naphthyl)-4-carbonyl-α-methyl cinnamic acid (obtained in Example XVIII) in 100 cm³ of anhydrous dimethylformamide, stirred at ambient temperature, 2.8 g of N,N'-carbonyldiimidazole are added.

The mixture is then stirred for three hours at a temperature of approximately 50° C. and then cooled to 0° C., at which temperature 4.5 cm³ of anhydrous ethylamine are slowly added. After stirring for one hour the reaction mixture is left overnight at ambient temperature. It is then poured over 200 cm³ of water and then extracted three times with the aid of 100 cm³ of ethyl acetate.

The ethyl acetate phases are combined, washed with a solution of ammonium chloride and then water and finally dried with magnesium sulfate. After evaporation of the ethyl acetate, the resulting crude product is purified by passage in a silica gel column and eluted with a 9 to 1 mixture of methylene and ethyl acetate.

After distillation of the eluant under reduced pressure and crystallization in hexane, 1.9 g of N-ethyl trans-5,5,8,8-tetramethyl-5,6,7,8-tetrahydro-2-naphthyl)-4-carbonyl-α-methyl cinnamide are obtained in the form of a yellow powder; melting point: 121° C.

Elemental analysis: $C_{27}H_{33}NO_2$; Calculated: C: 80.36; H: 8.24; N: 3.47; O: 7.93. Found: C: 80.27; H: 8.33; N: 3.40; O: 8.08.

EXAMPLE XXVI

Preparation of N-ethyl(5,5,8,8-tetramethyl-5,6,7,8-tetrahydro-2-naphthyl)-4-carbonyl benzamide Compound of formula II, in which: $A=-(CH_2)_2$, $R_1=R_2=R_3=R_4=CH_3$, R' and R"=oxo and $R=-CONHEt$.

In a first step, the chloride of N-ethyl-4-carbamoyl benzoic acid is prepared, by bringing to a boil a solution of 2 g of this acid in 50 cm³ of thionyl chloride over the course of 4 hours.

The thionyl chloride is then eliminated by evaporation under a vacuum.

2.2 g of crude acid chloride are converted directly by adding to the latter 1.76 g of 5,5,8,8-tetramethyl-5,6,7,8-tetrahydronaphthalene, diluted in 40 cm³ of anhydrous 1,2-dichloroethane.

To the mixture stirred at 0° C., in an inert atmosphere, 1.9 g of aluminum trichloride are added. Stirring is continued at this temperature for 3 hours and then at ambient temperature for 5 hours.

The reaction mixture is then poured into 200 cm³ of ice water and extracted three times with 100 cm³ of dichloroethane. The organic phases are combined, washed with an aqueous solution of aluminum chloride and then with water and finally dried with magnesium sulfate. After evaporation of the solvent, 3.6 g of crude product are obtained. The expected product is purified by silica gel chromatography. It is eluted with a 4-4-2 mixture of toluene, methylene chloride and ethyl acetate and then recrystallized in a mixture of hexane and isopropyl ether. 0.500 g of N-ethyl (5,5,8,8-tetramethyl-5,6,7,8-tetrahydro-2-naphthyl)-4-carbonyl benzamide is obtained, in the form of white crystals having a melting point of 102° C.

Elemental analysis: $C_{24}H_{29}NO_2$; Calculated: C: 79.30; H: 8.04; N: 3.85; O: 8.81. Found: C: 79.74; H: 7.94; N: 3.67; O: 8.77.

EXAMPLES OF COMPOSITIONS A. FOR ORAL ADMINISTRATION

| Example 1 - 0.2 g tablets | |
|---|---|
| (5,5,8,8-tetramethyl-5,6,7,8-tetrahydro-2-naphthyl)-4-carbonyl benzoic acid | 0.010 g |
| starch | 0.115 g |
| dicalcium phosphate | 0.020 g |
| silica | 0.020 g |
| lactose | 0.030 g |
| talc | 0.010 g |
| magnesium stearate | 0.005 g |

| Example 2 - drinkable suspension in 5 ml ampoules | |
|---|---|
| (1,1,2,3,3-pentamethyl-5-indanyl)-4-carbonyl benzoic acid | 0.010 g |

| Example 2 - drinkable suspension in 5 ml ampoules | |
| --- | --- |
| glycerin | 0.500 g |
| sorbitol, 70% | 0.500 g |
| sodium saccharinate | 0.010 g |
| methyl parahydroxybenzoate | 0.040 g |
| flavoring | q.s |
| purified water, qsp | 5.000 g |

In this example, the active compound can be repleaced with the same quantity of trans-(1,1,2,3,3-pentamethyl-5-indanyl)-4-carbonyl-α-methyl cinnamic acid.

B. TOPICAL APPLICATION

| Example 3 - ointment | |
| --- | --- |
| ethyl (1,1,2,3,3-pentamethyl-5-indanyl)-4-carbonyl-α-methyl cinnamate | 0.010 g |
| liquid petrolatum oil | 9.100 g |
| silica, sold by the Degussa corporation under the name "Aerosil 200" | 9.100 g |
| isopropyl myristate, qsp | 100.000 g |

In this example, the active compound can be replaced with the same quantity of (5,5,8,8-tetramethyl-5,6,7,8-tetrahydro-2-naphthyl)-4-carbonyl benzoic acid.

| Example 4 - anionic oil-in-water cream | |
| --- | --- |
| N—ethyl-(1,1,2,3,3-pentamethyl-5-indanyl)-4-carbonyl benzamide | 0.100 g |
| sodium dodecyl sulfate | 0.800 g |
| glycerol | 2.000 g |
| stearyl alcohol | 20.000 g |
| triglycerides of capric/caprylic acid sold by the Dynamit Nobel corporation under the name "Miglyol 812" | 20.000 g |
| preservatives | q.s |
| demineralized water, qsp | 100.000 g |

In this example, the active compound can be replaced with the same quantity of the following compound: trans-(5,5,8,8-tetramethyl-5,6,7,8-tetrahydro-2-naphthyl)-4-carbonyl cinnamic acid.

| Example 5 - gel | |
| --- | --- |
| N—ethyl-(1,1,2,3,3-pentamethyl-5-indanyl)-4-carbonyl benzamide | 5.000 g |
| hydroxypropyl cellulose, sold by the Hercules corporation under the name of "Klucel HF" | 2.000 g |
| water/ethanol (50/50), qsp | 100.000 g |

In this example, the active compound can be replaced with 0.05 g of trans-(5,5,8,8-tetramethyl-5,6,7,8-tetrahydro-2-naphthyl)-4-hydroxymethyl cinnamic acid or with 0.1 g of N-ethyltrans-(5,5,8,8-tetramethyl-5,6,7,8-tetrahydro-2-naphthyl)-4-carbonyl methylcinnamide.

| Example 6 - anti-seborrheic cream | |
| --- | --- |
| polyoxyethylenated stearate (40 moles of ethylene oxide) sold by the Atlas corporation under the name of "Myrj 52" | 4.000 g |
| mixture of lauric esters of sorbitol and sorbitan, polyoxyethylenated with 20 moles of ethylene oxide, sold by the Atlas corporation under the name "Tween 20" | 1.800 g |
| mixture of glycerol mono- and distearate sold by the Gattefosse corporation under the name "Geleol" | 4.200 g |
| propylene glycol | 10.000 g |
| butylhydroxyanisole | 0.010 g |
| butylhydroxytoluene | 0.020 g |
| keto-stearyl alcohol | 6.200 g |
| preservatives | q.s |
| perhydrosqualene | 18.000 g |
| mixture of caprylic/capric acid triglycerides sold by the Dynamit Nobel corporation under the name of "Miglyol 812" | 4.000 g |
| S—carboxymethylcysteine | 3.000 g |
| triethanolamine, 99% | 2.500 g |
| (1,1,2,3,3-pentamethyl-5-indanyl)-4-hydroxymethyl benzoic acid | 0.100 g |
| water, qsp | 100.000 g |

| Example 7 - anti-seborrheic cream | |
| --- | --- |
| polyoxyethylene stearate (40 moles of ethylene oxide) sold by the Atlas corporation under the name of "Myrj 52" | 4.000 g |
| mixture of lauric esters of sorbitol and sorbitan, polyoxyethylenated with 20 moles of ethylene oxide, sold by the Atlas corporation under the name "Tween 20" | 1.800 g |
| mixture of glycerol mono- and distearate sold by the Gattefosse corporation under the name "Geleol" | 4.200 g |
| propylene glycol | 10.000 g |
| butylhydroxyanisole | 0.010 g |
| butylhydroxytoluene | 0.020 g |
| keto-stearyl alcohol | 6.200 g |
| preservatives | qs |
| perhydrosqualene | 18.000 g |
| mixture of caprylic/capric acid triglycerides sold by the Dynamit Nobel corporation under the name of "Miglyol 812" | 4.000 g |
| 5-amino-5-carboxy-3-thiapentanoate of 2-benzylthio ethylammonium | 3.000 g |
| (5,5,8,8-tetramethyl-5,6,7,8-tetrahydro-2-naphthyl)-4-hydroxymethyl benzoic acid | 0.500 g |
| water, qsp | 100.000 g |

| Example 8 - hair lotion | |
| --- | --- |
| propylene glycol | 20.000 g |
| ethanol | 34.870 g |
| polyethylene glycol, molecular mass 400 | 40.000 g |
| water | 4.000 g |
| butylhydroxyanisole | 0.010 g |
| butylhydroxytoluene | 0.020 g |
| (5,5,8,8-tetramethyl-5,6,7,8-tetrahydro-2-naphthyl)-4-hydroxymethyl benzoic acid | 0.100 g |
| Minoxidil | 1.000 g |

In this example, the active compound can be replaced with 0.05 g of one of the following compounds: N-ethyl-trans-(5,5,8,8-tetramethyl-5,6,7,8-tetrahydro-2-naphthyl)-4-carbonyl-α-methylcinnamide or trans-(5,5,8,8-tetramethyl-5,6,7,8-tetrahydro-2-naphthyl)-4-hydroxymethyl cinnamic acid.

| Example 9 - anti-acne gel | |
| --- | --- |
| (1,1,2,3,3-pentamethyl-5-indanyl)-4-carbonyl benzoic acid | 0.010 g |
| isopropyl alcohol | 40.000 g |
| acrylic acid polymer sold by the Goodrich Chemical Company under the name "Carbopol 940" | 1.000 g |
| triethanolamine, 99% | 0.600 g |
| butylhydroxyanisole | 0.010 g |
| butylhydroxytoluene | 0.020 g |
| tioxolone | 0.500 g |

| Example 9 - anti-acne gel | |
| --- | --- |
| propylene glycol | 8.000 g |
| purified water, qsp | 100.000 g |

In this example, the active compound may be replaced with the same quantity of N-ethyl-trans-(5,5,8,8-tetramethyl-5,6,7,8-tetrahydro-2-naphthyl)-4-carbonylmethyl cinnamide or by 0.1 g of trans-(5,5,8,8-tetramethyl-5,6,7,8-tetrahydro-2-naphthyl)-4-carbonyl cinnamic acid.

We claim:

1. Bicyclic aromatic compound, having the formula

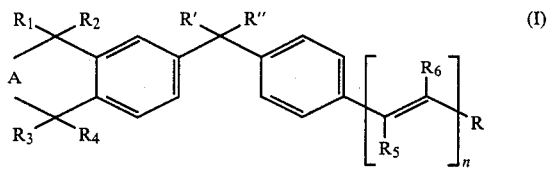

in which
n=0 or 1,
R' represents hydrogen, OH, alkoxy having from 1 to 4 carbon atoms, or acyloxy having from 1 to 4 carbon atoms;
R" represents hydrogen or alkoxy having from 1 to 4 carbon atoms;
or R' and R" taken together form an oxo (=O), methano (=CH$_2$) or hydroxyimino (=N—OH) radical;
R represents —CH$_2$OH or —COR$_7$;
R$_7$ represents hydrogen, —OR$_8$ or

in which R$_8$ represents hydrogen, alkyl having from 1 to 20 carbon atoms, monohydroxyalkyl, polyhydroxyalkyl phenyl, phenyl substituted with at least one halogen atom, —OH, —NO$_2$, lower alkyl having 1-6 carbon atoms, trifluoromethyl or a carboxylic acid function, benzyl, phenethyl, a residue of glucose, mannose, erythrose or galactose, or

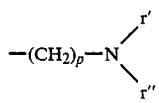

where p is 1, 2 or 3 and r' and r" represent hydrogen, lower alkyl having 1-6 carbon atoms, monohydroxyalkyl monohydroxyalkyl interrupted by a heteroatom, polyhydroxyalkyl, aryl or benzyl, amino acid residue, a residue of glucosamine, galactosamine, mannosamine or meglumine or when taken together with the nitrogen atom to which they are attached form a heterocycle;
A represents methylene or dimethylene, unsubstituted or substituted with lower alkyl having 1-6 carbon atoms;
R$_1$, R$_2$, R$_3$ and R$_4$ represent hydrogen or lower alkyl having 1-6 carbon atoms;
R$_1$ and R$_3$ taken together are capable of forming a methylene or dimethylene radical, A representing a dimethylene radical;
R$_5$ and R$_6$ represent hydrogen or methyl;
and the salts of said compound, as well as their optical and geometric isomers.

2. The compound of claim 1, wherein R$_8$ is selected from the group consisting of methyl, ethyl, isopropyl, butyl, tert. butyl, 2-ethylhexyl, isooctyl, dodecyl, hexadecyl and octadecyl.

3. The compound of claim 1, wherein said monohydroxyalkyl is 2-hydroxyethyl, 2-hydroxypropyl or 2-hydroxyethoxyethyl.

4. The compound of claim 1, wherein said polyhydroxyalkyl is 2,3-dihydroxypropyl, 1,3-dihydroxy-2-propyl or pentaerythritol residue.

5. The compound of claim 1, wherein said alkoxy is methoxy, isopropoxy, butoxy or tert. butoxy.

6. The compound of claim 1, wherein r' and r" taken together with the nitrogen atom to which they are attached form a piperidino, piperazino, morpholino, pyrrolidino or 4-(2-hydroxyethyl) piperazino radical.

7. The compound of claim 1 having the formula:

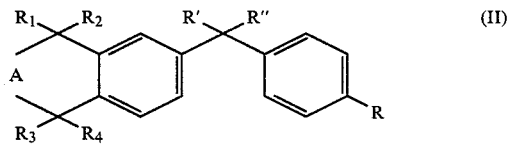

in which:
A, R, R$_1$-R$_4$, R' and R" have the same meanings as those provided in claim 1.

8. The compound of claim 1 having the formula:

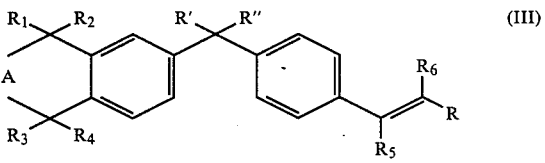

in which:
A, R, R$_1$-R$_6$, R' and R" have the same meanings as those provided in claim 1.

9. The compound of claim 1 having the formula

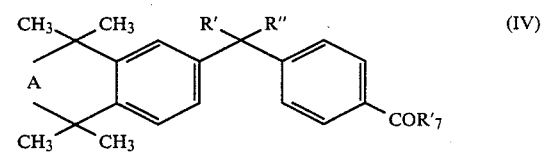

in which
A represents CH$_3$—CH< or dimethylene;
R' represents OH and R" represents hydrogen, or R' and R", taken together, form an oxo radical (=O);
and R'$_7$ represents hydrogen, —OR'$_8$, or

R'$_8$ represents hydrogen or lower alkyl having 1-6 carbon atoms;

r' represents hydrogen and r" represents lower alkyl having 1-6 carbon atoms or a substituted phenyl radical, or r' and r" taken together with the nitrogen atom to which they are attached form 4-(2-hydroxyethyl) piperazino.

10. The compound of claim 1 having the formula

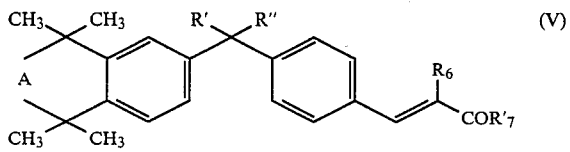

in which:

A represents CH$_3$—CH< or dimethylene,
R' represents OH and R" represents hydrogen, or R' and R", taken together, form an oxo radical (=O);
R$_6$ represents hydrogen or methyl,
and R'$_7$ represents —OR'$_8$ or

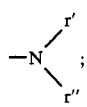

R'$_8$ represents hydrogen or lower alkyl having 1-6 carbon atoms;
r' represents hydrogen and r" represents lower alkyl having 1-6 carbon atoms.

11. The compound of claim 1 selected from the group consisting of:

(1) (5,5,8,8-tetramethyl-5,6,7,8-tetrahydro-2-naphthyl)-4-carbonyl methyl benzoate;
(2) (5,5,8,8-tetramethyl-5,6,7,8-tetrahydro-2-naphthyl)-4-carbonyl benzoic acid;
(3) (5,8-methano-5,6,7,8-tetrahydro-2-naphthyl)-4-carbonyl benzaldehyde;
(4) (5,5,8,8-tetramethyl-5,6,7,8-tetrahydro-2-naphthyl)-4-carbonyl benzaldehyde;
(5) (1,1,2,3,3-pentamethyl-5-indanyl)-4-carbonyl methyl benzoate;
(6) (1,1,2,3,3-pentamethyl-5-indanyl)-4-carbonyl benzoic acid;
(7) (1,1,2,3,3-pentamethyl-5-indanyl)-4-carbonyl benzaldehyde;
(8) 1-(1,1,2,3,3-pentamethyl-5-indanyl)-1-(4-hydroxymethylphenyl) methanol;
(9) (5,5,8,8-tetramethyl-5,6,7,8-tetrahydro)-2-naphthyl-4-hydroxymethyl benzoic acid;
(10) (1,1,2,3,3-pentamethyl-5-indanyl)-4-hydroxymethyl benzoic acid;
(11) (1,1,2,3,3-pentamethyl-5-indanyl)-4-hydroxymethylmethyl benzoate;
(12) N-ethyl(5,5,8,8-tetramethyl-5,6,7,8-tetrahydro-2-naphthyl)-4-carbonyl benzamide;
(13) N-ethyl(1,1,2,3,3-pentamethyl-5-indanyl)-2-carbonyl benzamide;
(14) ethyl trans-(5,8-methano-5,6,7,8-tetrahydro-2-naphthyl)-4-carbonyl cinnamate;
(15) trans-(5,8-methano-5,6,7,8-tetrahydro-2-naphthyl)-4-carbonyl cinnamic acid;
(16) ethyl trans-(5,5,8,8-tetramethyl-5,6,7,8-tetrahydro-2-naphthyl)-4-carbonyl cinnamate;
(17) trans-(5,5,8,8-tetramethyl-5,6,7,8-tetrahydro-2-naphthyl)-4-carbonyl cinnamic acid;
(18) ethyl trans-(5,5,8,8-tetramethyl-5,6,7,8-tetrahydro-2-naphthyl)-4-carbonyl-α-methyl cinnamate;
(19) trans-(5,5,8,8-tetramethyl-5,6,7,8-tetrahydro-2-naphthyl)-4-carbonyl-α-methyl cinnamic acid;
(20) ethyl trans-(1,1,2,3,3-pentamethyl-5-indanyl)-4-carbonyl-α-methyl cinnamate;
(21) trans-(1,1,2,3,3-pentamethyl-5-indanyl)-4-carbonyl-α-methyl cinnamic acid;
(22) ethyl trans-(5,5,8,8-tetramethyl-5,6,7,8-tetrahydro-2-naphthyl)-4-hydroxymethyl-α-methyl cinnamate;
(23) trans-(5,5,8,8-tetramethyl-5,6,7,8-tetrahydro-2-naphthyl)-4-hydroxymethyl-α-methyl cinnamic acid;
(24) N-ethyl-trans-(5,5,8,8-tetramethyl-5,6,7,8-tetrahydro-2-naphthyl)-4-hydroxymethyl-α-methyl cinnamide;
(25) N-ethyl-trans-(5,5,8,8-tetramethyl-5,6,7,8-tetrahydro-2-naphthyl)-4-carbonyl-α-methyl cinnamide;
(26) N-ethyl-trans-(1,1,2,3,3-pentamethyl-5-indanyl)-4-carbonyl-α-methyl cinnamide;
(27) ethyl trans-(5,5,8,8-tetramethyl-5,6,7,8-tetrahydro-2-naphthyl)-4-hydroxymethyl cinnamate;
(28) trans-(5,5,8,8-tetramethyl-5,6,7,8-tetrahydro-2-naphthyl)-4-hydroxymethyl cinnamic acid;
(29) 4'-(2-hydroxyethyl)piperazino(5,5,8,8-tetramethyl-5,6,7,8-tetrahydro-2-naphthyl) 4-carbonyl benzamide;
(30) N-(3,5-di-trifluoromethyl-1-phenyl)-(5,5,8,8-tetramethyl-5,6,7,8-tetrahydro-2-naphthyl)-4-carbonyl benzamide.

12. A method for preparing the compound of claim 1 comprising reacting an acid chloride having the formula,

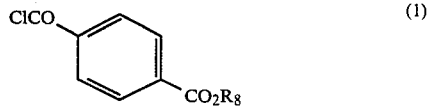

in an organic solvent medium with an aromatic compound having one of the following formulas:

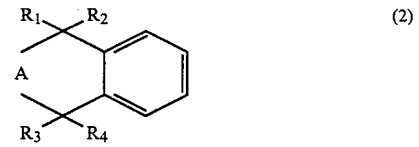

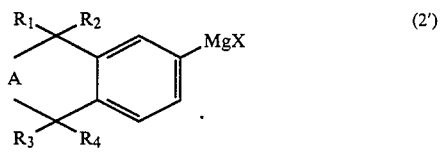

in which:

A, R$_1$–R$_4$ have the same meanings as those given in claim 1, R$_8$ being alkyl having from 1 to 20 carbon atoms, and X is Br or Cl, and optionally saponifying the resulting ketonic ester to the corresponding ketonic acid, and subsequently converting the said ketonic acid to the corresponding amide by the reaction with an amine having the formula:

in which:

r' and r" have the same meanings as those given in claim 1, or subsequently converting said ketonic acid to a hydroxy acid or to a diol with the optional oxidation of said diol to the corresponding ketonic aldehyde.

13. The method of claim 12, wherein the condensation reaction of said aromatic compound (2) is performed in the presence of anhydrous aluminum chloride in 1,2-dichloroethane at a temperature ranging from 0° to 25° C., while stirring the reaction mixture.

14. The method of claim 12, wherein the condensation of said acid chloride with the magnesium salt of formula (2') is performed at a temperature of about 0° C. in THF.

15. The method of claim 12, wherein the preparation of the amide is carried out in the presence of N,N'-carbonyl diimidazole.

16. The method of claim 12, wherein the reduction of the ketonic acid to the corresponding hydroxy acid is performed in the presence of sodium borohydride in THF.

17. The method of claim 12, wherein the ketonic aldehyde is obtained by oxidation of said diol using pyridinium chlorochromate, said corresponding diol resulting from a reduction reaction of said ketonic acid in the presence of aluminum lithium hydride.

18. A method of preparing the compound of formula I of claim 1 wherein n=0 and R=CHO, comprising reacting an acid chloride having the formula:

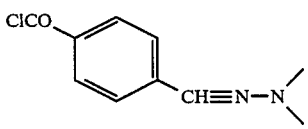

in an organic solvent medium, under Friedel-Crafts reaction conditions with an aromatic compound having the formula:

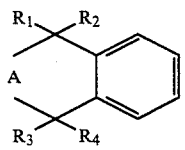

and liberating the aldehyde function by exchange with the glyoxal so as to obtain the expected ketonic aldehyde.

19. A method for preparing a compound having the formula:

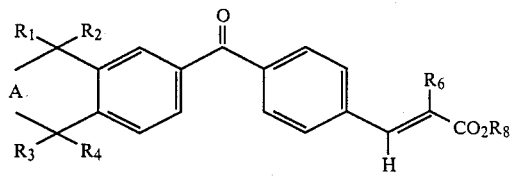

in which:
$R_1$–$R_4$, $R_6$ and $R_8$ have the same meanings as in claim 1 comprising reacting a ketonic aldehyde having the formula:

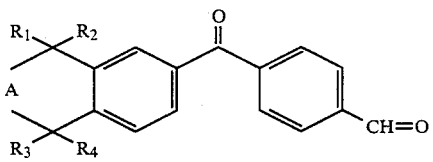

in which:
A and $R_1$–$R_4$ have the same meanings as in claim 1, with an alkyl phosphonoacetate having the formula:

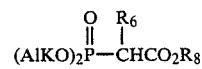

in the presence of sodium hydride in THF, and subjecting the resulting unsaturated keto ester to conventional reaction conditions so as to obtain the radicals in formula (I) given in claim 1.

20. A medicine comprising a compound of formula (I), as defined in claim 1 and a pharmaceutically acceptable vehicle.

21. The medicine of claim 20, administered in a daily dose of about 2 µg/kg to 2 mg/kg of body weight.

22. A pharmaceutical composition, comprising in a pharmaceutically acceptable vehicle, for enteral, parenteral, topical or ocular administration, at least one compound of formula (I) defined in claim 1.

23. The pharmaceutical composition of claim 22, in a form appropriate for topical or ocular application, said composition containing from 0.0005 to about 5% by weight of said compound based on the total weight of said composition.

24. A cosmetic composition for body and hair hygiene comprising in a cosmetically acceptable vehicle, at least one compound of formula (I) as defined in claim 1.

25. The cosmetic composition of claim 24, wherein said compound of formula (I) is present in an amount ranging from 0.0005 and 2% by weight, based on the total weight of said composition.

26. Trans-(5,5,8,8-tetramethyl-5,6,7,8-tetrahydro-2-naphthyl)-4-carbonyl-α-methylcinnamic acid.

27. A medicine comprising the compound of claim 26 and a pharmaceutically acceptable vehicle.

28. A pharmaceutical composition comprising in a pharmaceutically acceptable vehicle, for enteral, parenteral, topical or ocular administration, the compound of claim 26.

29. A cosmetic composition for body or hair hygiene comprising in a cosmetically acceptable vehicle, the compound of claim 26.

* * * * *